(12) United States Patent
Gorsuch et al.

(10) Patent No.: US 7,354,392 B2
(45) Date of Patent: *Apr. 8, 2008

(54) STRUCTURALLY OPTIMIZED HOLLOW FIBER MEMBRANES

(75) Inventors: Reynolds G. Gorsuch, Yountville, CA (US); Harold W. Peters, Martinez, CA (US); Harold H. Handley, Jr., Novato, CA (US)

(73) Assignee: Transvivo Inc., Richmond, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 10/786,339

(22) Filed: Feb. 25, 2004

(65) Prior Publication Data

US 2005/0187508 A1  Aug. 25, 2005

(51) Int. Cl.
*A61M 25/14* (2006.01)
(52) U.S. Cl. ............ 600/6.04; 604/6.09; 210/321.88
(58) Field of Classification Search ........... 604/6.04, 604/6.09, 6.16, 4.01; 210/321.88, 483
See application file for complete search history.

(56) References Cited

U.S. PATENT DOCUMENTS

| | | | | |
|---|---|---|---|---|
| 2,742,931 A | * | 4/1956 | De Ganahl | 138/144 |
| 3,156,598 A | * | 11/1964 | Martin | 156/161 |
| 3,177,902 A | * | 4/1965 | Rubenstein | 138/176 |
| 3,249,481 A | * | 5/1966 | Boggs | 156/172 |
| 3,494,121 A | | 2/1970 | Bohrer | |
| 4,402,830 A | * | 9/1983 | Pall | 210/457 |
| 4,440,641 A | * | 4/1984 | Ostertag | 210/321.79 |
| 4,454,085 A | * | 6/1984 | Schindler et al. | 264/41 |
| 4,481,260 A | * | 11/1984 | Nohmi | 428/398 |
| 4,769,146 A | * | 9/1988 | Schmidt | 210/321.8 |
| 4,832,034 A | | 5/1989 | Pizziconi et al. | 128/632 |
| 4,882,223 A | | 11/1989 | Aptel et al. | 210/500.22 |
| 4,935,141 A | | 6/1990 | Buck et al. | 210/500.38 |
| 4,950,224 A | | 8/1990 | Gorsuch et al. | 604/4 |
| 5,145,583 A | | 9/1992 | Angleraud et al. | 210/646 |
| 5,151,082 A | | 9/1992 | Gorsuch et al. | 604/4 |
| 5,152,743 A | | 10/1992 | Gorsuch et al. | 604/4 |
| 5,224,926 A | | 7/1993 | Gorsuch et al. | 604/4 |
| 5,284,583 A | * | 2/1994 | Rogut | 210/321.8 |
| 5,605,627 A | | 2/1997 | Carlsen et al. | 210/321.79 |
| 5,706,806 A | * | 1/1998 | Kissinger | 600/309 |
| 5,735,809 A | | 4/1998 | Gorsuch | 604/4 |

(Continued)

FOREIGN PATENT DOCUMENTS

EP    0 801 973 A1    10/1997

(Continued)

OTHER PUBLICATIONS

Handley, Harold H., et al., Intravenous Catheter for Intracorporeal Plasma Filtration, Jan. 24, 2002, Blood Purification 2000, 20:61-69.*

*Primary Examiner*—Tatyana Zalukaeva
*Assistant Examiner*—Paula L Craig
(74) *Attorney, Agent, or Firm*—Knobbe Martens Olson & Bear LLP

(57) ABSTRACT

An elongated hollow microporous fiber comprises an inner wall surface defining an interior fiber lumen, an outer wall surface, and a microporous fiber wall therebetween, the fiber wall having one or more continuous, cohesive, elongated filaments embedded in the fiber and extending lengthwise of the elongated fiber along substantially the full length of the fiber.

29 Claims, 4 Drawing Sheets

U.S. PATENT DOCUMENTS

| | | | |
|---|---|---|---|
| 5,762,798 A | 6/1998 | Wenthold et al. | 210/500.23 |
| 5,788,661 A * | 8/1998 | Japuntich | 604/6.09 |
| 5,800,525 A * | 9/1998 | Bachinski et al. | 623/1.1 |
| 5,834,583 A | 11/1998 | Hancock et al. | 528/499 |
| 5,846,422 A | 12/1998 | Ditter et al. | 210/500.41 |
| 5,897,729 A * | 4/1999 | Bikson et al. | 156/172 |
| 5,968,004 A * | 10/1999 | Gorsuch | 604/6.04 |
| 5,980,478 A | 11/1999 | Gorsuch et al. | 604/4 |
| 6,013,182 A * | 1/2000 | Emi et al. | 210/500.23 |
| 6,258,272 B1 | 7/2001 | Wang et al. | 210/500.41 |
| 6,561,996 B1 * | 5/2003 | Gorsuch | 604/6.09 |
| 6,607,501 B2 * | 8/2003 | Gorsuch | 604/5.01 |
| 6,659,973 B2 * | 12/2003 | Gorsuch et al. | 604/6.04 |
| 6,802,820 B1 * | 10/2004 | Gorsuch et al. | 604/6.04 |
| 6,802,971 B2 * | 10/2004 | Gorsuch et al. | 210/500.23 |
| 6,849,183 B2 * | 2/2005 | Gorsuch et al. | 210/646 |
| 6,899,692 B2 * | 5/2005 | Gorsuch et al. | 604/6.09 |
| 7,267,771 B2 * | 9/2007 | Gorsuch et al. | 210/321.88 |
| 2002/0046970 A1 | 4/2002 | Murase et al. | |
| 2002/0087109 A1 * | 7/2002 | Gorsuch et al. | 604/6.04 |
| 2002/0188240 A1 * | 12/2002 | Gorsuch | 604/6.04 |
| 2003/0073946 A1 | 4/2003 | Gorsuch et al. | |
| 2003/0153943 A1 * | 8/2003 | Michael et al. | 606/200 |
| 2003/0236482 A1 * | 12/2003 | Gorsuch et al. | 604/6.04 |
| 2004/0034317 A1 * | 2/2004 | Gorsuch et al. | 604/5.01 |
| 2004/0050788 A1 | 3/2004 | Gorsuch et al. | 210/645 |
| 2005/0155932 A1 * | 7/2005 | Gorsuch et al. | 210/650 |
| 2005/0215936 A1 * | 9/2005 | Gorsuch et al. | 604/6.01 |
| 2006/0015136 A1 * | 1/2006 | Besselink | 606/200 |
| 2006/0106331 A1 * | 5/2006 | Gorsuch et al. | 604/6.09 |
| 2006/0124530 A1 * | 6/2006 | Gorsuch et al. | 210/321.88 |

FOREIGN PATENT DOCUMENTS

| | | |
|---|---|---|
| EP | 0 882 494 A1 | 12/1998 |
| EP | 0 998 972 A | 5/2000 |
| FR | 2566003 | 12/1995 |
| GB | 1 374 704 A | 11/1974 |
| JP | 9323031 | 12/1997 |
| WO | WO 01/78805 A1 | 10/2001 |
| WO | WO 2004/009221 | 1/2004 |

* cited by examiner

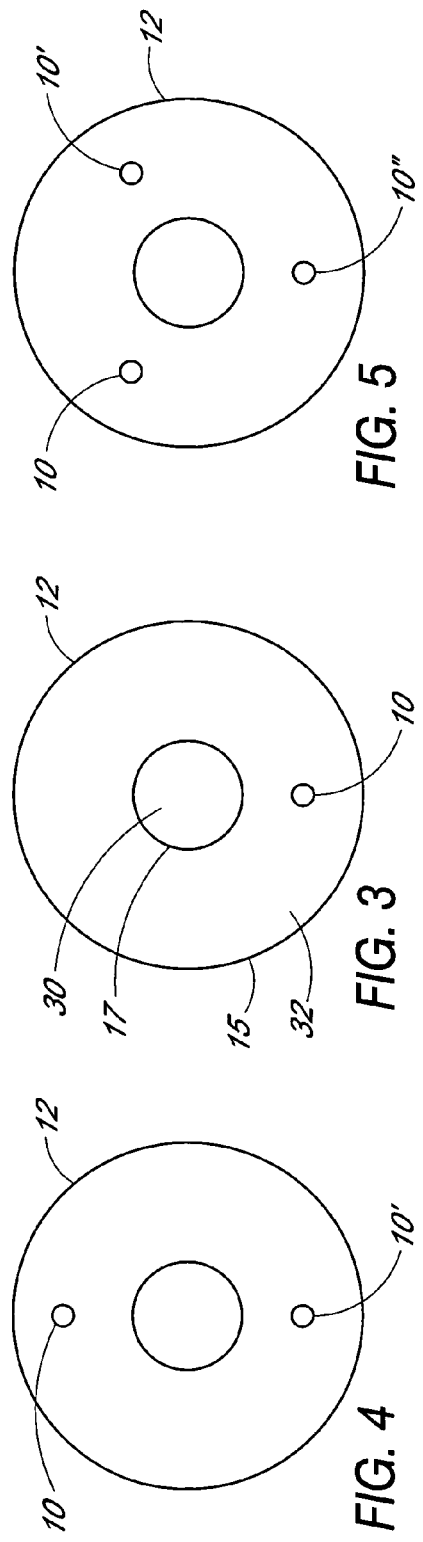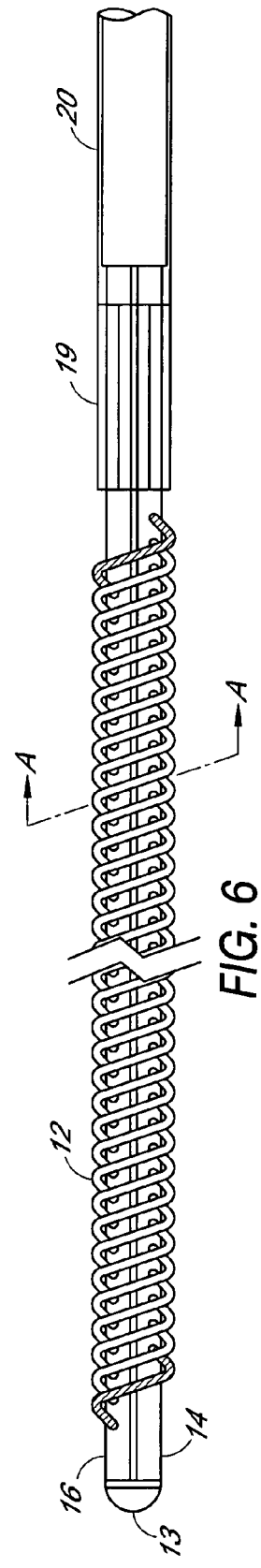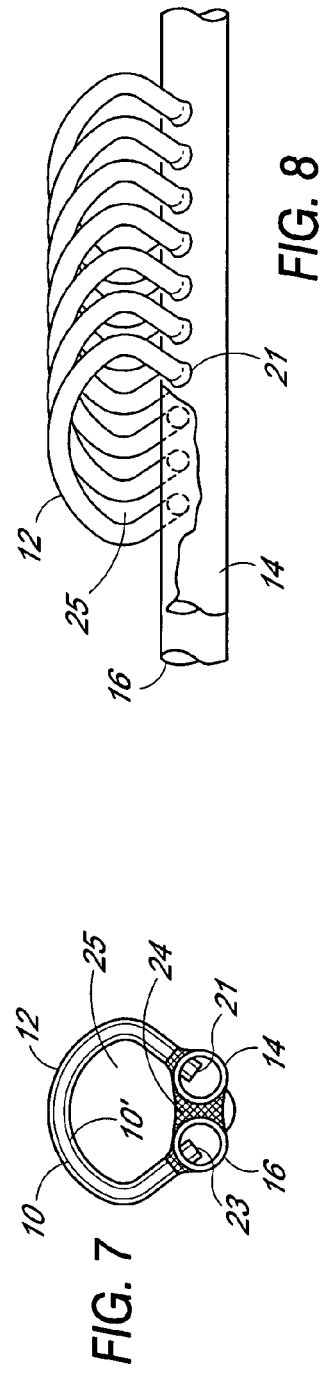

STRUCTURALLY OPTIMIZED HOLLOW FIBER MEMBRANES

BACKGROUND OF THE INVENTION

In U.S. Pat. Nos. 4,950,224, 5,152,743, 5,151,082, 5,735,809, 5,968,004 and 5,980,478 there are disclosed methods and apparatus for carrying out in-vivo plasmapheresis for separating plasma from other blood components within the body and blood vessels of the patient. Blood plasma and/or selected plasma components separated from whole blood in-vivo by hollow fiber membranes is pumped from the patient via a catheter placed in the superior vena cava to a treatment means such as a dialyzer apparatus, adsorption column, or selective separation apparatus in which toxic metabolic waste products, specific proteins, or other elements in the plasma are removed or treated. After the plasma is treated for removal or recomposition of waste products, water or excess fluids, toxins, and/or deleterious plasma proteins, the treated plasma is returned and reintroduced to the patients' blood stream. The methods and apparatus described in the aforesaid patents are incorporated herein by reference. In U.S. Pat. Nos. 6,607,501, and 6,632,192 these membranes and catheter systems are utilized for providing metabolic support for tissue engineering devices and systems as well as for the selective reduction of segmental intracellular and extracellular edema.

Methods of plasma and toxin removal from blood as taught by the above patents are unique and substantially superior to conventional means of hemodialysis as presently practiced for both acute and chronic kidney failure as well as for therapeutic apheresis applications, primarily because removal of whole blood from the patient's vasculature and treatment of the blood ex-vivo is eliminated from the procedure. In conventional hemodialysis procedures hollow fiber membranes are used in the ex-vivo dialysis and hemo-filter cartridges for blood purification and in therapeutic apheresis applications and tissue engingeering applications blood is separated ex-vivo by centrifugation. In hemodialysis procedures the blood is routed from the patient and directed through the center lumen of the hollow fibers in the ex-vivo cartridges while dialysate fluid passes over the outside walls of the fibers within the cartridge cavity in counter-flow direction to blood flow whereby blood toxins are diffused through the fiber membrane and/or water is removed by conductive means. Thus, in hemodialysis toxin diffusion and ultrafiltration are from inside the fiber lumen to a compartment outside the fiber walls where the ultrafiltrate and toxin-saturated dialysate are collected for further processing and/or disposal.

Conventional hollow fiber membranes commercially used for present hemodialysis, hemo-ultrafiltration, and dialyzer cartridges fabricated from proprietary and non-proprietary polymer compositions have symmetrical or asymmetrical fiber wall morphology. The cellular structure and porosity of the fiber wall generally is uniform from the inner lumen to the outside membrane surface. In asymmetrical compositions, both morphology and pore structures vary from the inner lumen to the outer surface cartridges. Conventional hollow fibers or filter membranes are unable to successfully perform in-vivo, intravascular plasma separation because these commercial membranes generally have poor structural strength, acceptable in an encapsulated device external to the body but not acceptable for an in-vivo placement for safety reasons. Further the actual filtration surface of these conventional dialysate hollow fiber membrane filters is on or close to the surface of the inner lumen of these membranes and can not perform satisfactorily in a demanding in-vivo environment of relatively high flow rate of blood at the exterior fiber surface where the filtration surface of the subject filters reside and operate at relatively low lumen pressure and high blood flow rates. For example, typical in-vivo blood flow within a vena cava is about 2.5 L per minute, whereas blood flow through typical dialysate filter apparatus is nearly stagnant (2-300 ml/min/7,000 fibers=0.042 ml/m/fiber), e.g., about 0.42 ml per minute per fiber. Also the trans-membrane pressure (TMP) used in the subject membranes is typically about 50 mm Hg or less, as compared to TMP of 100-300 mm Hg as used in conventional extracorporeal dialysate filters.

In U.S. patent application Ser. No. 09/549,131 filed Apr. 13, 2000, (TRANSVI.007A) entitled "Specialized Hollow Fiber Membranes for In-Vivo Plasmapheresis and Ultrafiltration," there are disclosed elongated hollow microporous fibers having an asymmetrical fiber wall characterized by a lower mass density adjacent to the inner wall surface extending along the interior lumen of the fiber and a higher mass density adjacent to the outer wall surface. Such a fiber wall morphology and pore structure provide unique characteristics necessary for separating blood plasma and/or plasma water in-vivo where continuous extraction of cell-free plasma or ultrafiltered plasma water and its associated toxins is carried out within the blood vessel of a patient, human or animal. While the aforesaid disclosed fibers are orders of magnitude stronger than conventional fibers commonly used in ex-vivo systems, there exists the possibility of accidental breakage of the fibers during fiber or filter construction, or during insertion or implantation of a filter containing the fiber or under conditions of excessive, accidental, violent trauma experienced by a patient. The use of such fibers in a preferred filter device and catheter assembly are disclosed in U.S. patent application Ser. No. 09/981,783, filed Oct. 17, 2001 (TRANSVI.011A), the description thereof which is incorporated herein by reference, and will be further discussed hereinafter. The fibers are installed in the filter device such that each end of a hollow membrane is attached to the filter device with adhesive or suitable bonding material to prevent loss of the fiber from the assembly should the fiber break anywhere along its length. However, in an unlikely event that a fiber could be broken at two places along its length or at both ends and a portion of the fiber freed from attachment to the catheter, it could be carried by the blood to a patient's lungs with a possible deleterious effect.

SUMMARY OF THE INVENTION

The present invention is directed to elongated hollow microporous fibers having one or more filaments extending along the length of each fiber. In a preferred embodiment, one or more filaments are embedded in the microporous fiber wall between the inner fiber wall surface and the outer water surface. Preferably, the one or more filaments extend generally axially along the fiber length and substantially the entire length of the fiber. In a filter device incorporating the fibers containing the embedded filaments both ends of each fiber and the filaments are secured in the filter device.

BRIEF DESCRIPTION OF THE DRAWINGS

FIGS. 3, 4 and 5 are schematic end views of hollow fibers having one, two and three filaments embedded therein, respectively;

FIG. 6 is a top view of a preferred embodiment of a filter device incorporating elongated hollow fibers described herein with each end of a fiber secured to an elongated hollow tube;

FIG. 7 is an enlarged sectional view of the filter device of FIG. 6 along lines A-A showing a single elongated hollow fiber secured to the hollow tubes;

FIG. 8 is an enlarged side view of a portion of a filter device of the type illustrated in FIG. 6.

DETAILED DESCRIPTION OF THE PREFERRED EMBODIMENT

The hollow microporous fibers described herein are structurally enhanced or optimized by having one or more elongated filaments embedded in the fiber wall, and which filaments preferably extend substantially the entire length of the elongated fiber. The structurally and physically enhanced fibers incorporating the one or more filaments may be any elongated microporous fiber such as used for filtering fluids through the fiber wall. More specifically, the fibers to be enhanced are those which may be used for filtering plasma or plasma components from whole blood, and especially those fibers which are to be implanted in a patient's vasculature for in-vivo plasmapheresis or ultrafiltration. Such fibers and filters incorporating such fibers are described in U.S. Pat. Nos. 4,950,224; 5,151,082; 5,152,743; 5,224,926; 5,242,382; 5,735,809; 5,980,478 6,607,501 and 6,632,192, the descriptions of which are incorporated herein by reference.

Figure 1:
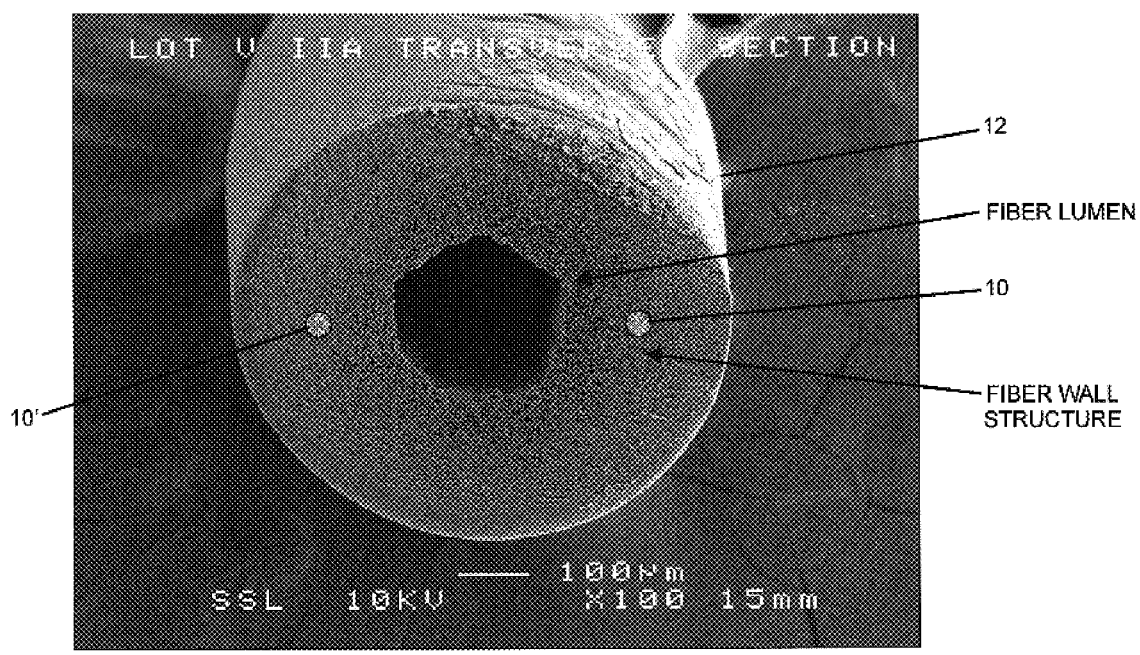
FIG. 1 is a scanning electron microscopy (SEM) image of a cross-section of a preferred fiber at 100 μm magnification and in which two filaments are embedded in the fiber wall between the inner and outer fiber wall surfaces.
Figure 2:
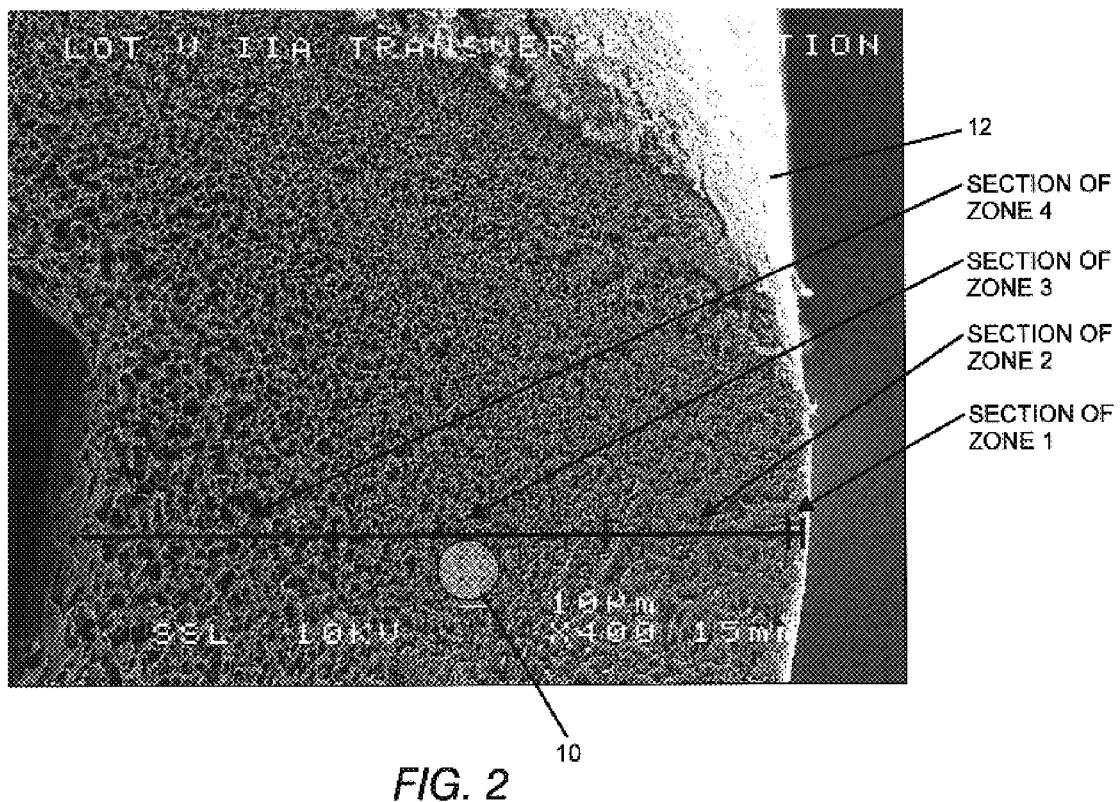
FIG. 2 is a SEM cross-section of a portion of the fiber at 400 μm magnification showing four zones of asymmetrical wall structure between the inner and outer fiber wall surfaces, and in which fiber wall a filament is embedded.

The fiber wall structure of the preferred elongated microporous fibers is asymmetrical between the inner wall surface extending along the interior fiber lumen and the outer fiber wall surface exposed to blood in the vessel in which the filter device is implanted. The fiber wall at or adjacent to the outer wall surface has a higher mass density than the mass density adjacent to or at the inner wall surface. The mass density is a function of the average nominal pore size. Such asymmetric fiber wall morphology is illustrated in FIGS. 1 and 2, FIG. 1 showing a scanning electron microscopy (SEM) image of a cross-section of the fiber at 100 μm magnification. FIG. 2 shows a portion of the FIG. 1 fiber wall cross-section at a magnification of 400 μm. The fiber wall comprises a pore and void structure defined within frames or solid walls which form boundaries of the pores. The pores are voids of variable definitive sizes which permit passage of fluid through the fiber wall to the lumen and which pores obstruct the passage of components larger than the pore diameter. The pores are irregular-shaped voids bounded by solid frames to form irregular tortuous paths for irregular and regular-shaped solutes. The wall structure of the fiber from the outer surface to the lumen is a continuum of voids bounded by solid frames with non-linear pore and void distribution. The resulting structure is a continuous change in mass density between the outer surface of the fiber and the inner lumen surface. However, it is convenient to describe the different mass density as sections or zones of the wall area having an average nominal pore size or average pore diameter, each zone having a different average nominal pore size. The walls may be characterized by two or more zones, for example 2, 3, or 4 or more mass density zones. In the fibers, the outer surface of the membrane, Zone 1, has the highest mass density characterized by smaller average pore diameters. The outer zone forms the fiber interface with the permeate blood flow by determining filtration characteristics including the composition and components of separated plasma and controlling fiber membrane performance. Thus, Zone 1 is the principle filtration portion of the fiber wall for controlling the trans-membrane flux (TMF) for excluding even the smallest cells in the blood, the platelets, having a diameter of about 1 μm. Nominal average pore diameters in Zone 1 are between about 0.3 μm and about 1 μm, and preferably range from about 0.4 μm to about 0.8 μm. A preferred filtration sizing has a cutoff of about 0.6 μm to about 0.8 μm. Zones 2 and 3 are designed to decrease the flow path tortuosity and maintain the structural integrity required of the fiber exposed to physical conditions within the body. Pore size distribution in these zones ranges gradually from about 0.8 μm to about 1.2 μm and from about 1.2 μm to about 2.0 μm. Zone 2, having some flux-controlling pores, is principally to provide structural strength to the fiber as well as acting as a conduit for exudate flow to Zone 3, also providing structure and enlarged pores for reducing the hydraulic resistance and providing a fluid conduit to the fiber lumen. The interior zones have little filtration function. Zone 4, representing the largest area having relatively large voids and pore diameters with little solid structure, has the primary function of a major reduction of hydraulic resistance through the membrane and defines the fiber inner lumen surface. Nominal average pore diameters in this lowest mass density zone are between about 1 μm and about 60 μm, and preferably between about 2 μm and about 6 μm. A typical fiber as shown has an OD of about 650 μm, an ID of about 250 μm and a wall thickness of about 250 μm. However, such dimensions are by way of example only. The hollow fibers shown in FIGS. 1 and 2 are also shown and described in more detail in the aforesaid application Ser. No. 09/549, 131 (TRANSVI.007A), the description of which is incorporated herein by reference.

The elongated microporous fibers used in the filter device may be produced using biocompatible polymers including those produced from polyurethanes, polypropylenes, polysulfones, polyethersulfones, polyesters, polycarbonates, nylons, polyimides, as well as other synthetic resins known to those skilled in the art. A preferred polymer is polysulfone, and more preferably a polyethersulfone/poly(ethylene oxide) copolymer with a poly(ethylene glycol) solvent or a polysulfone modified with poly(ethylene oxide)-poly(ethylene glycol) copolymer. Such polysulfone fibers are produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-methyl pyrrolidone, dimethyl acetomide, dimethyl sulfoxide, and mixtures of two or more such materials. Such polysulfone fibers have been found to have the least detrimental characteristics that influence protein membrane interaction such as crystallinity, ionic groups, hydrogen bonding groups and hydrophobic sites. Specific methods for producing the polymers and fibers are known to those skilled in the art and disclosed, for example, in PCT Publication WO 90/04609.

Referring to FIGS. 1-5, there are shown different views of a fiber 12 having one or more filaments 10 embedded in the fiber walls. As illustrated in FIG. 3, the fiber 12 has an outer fiber wall 15, an inner fiber wall 17 defining an inner fiber lumen 30, with the fiber wall 32 defined between the inner and outer fiber walls. Filament 10 is embedded in the fiber wall between the inner and outer fiber wall surfaces. In FIG. 4, two filaments 10 and 10' are shown and in FIG. 5 three filaments 10, 10' and 10" are shown. The filaments are preferably embedded uniformly between the inner and outer fiber walls along the full length of the fiber. It is also preferred that the one or more filaments be embedded in the fiber wall substantially equal distance between the inner wall surface and the outer wall surface, or in the middle of the fiber wall. The one or more filaments also preferably extend generally axially along the fiber length and coaxially with the interior fiber lumen. However, in some cases it may be desirable to extend one or more filaments helically or spirally along the length of the fiber.

A filament may comprise a single filament or strand thread of material, or woven, or twisted threads or strands of a filament or thread material. The filament may also be a single extruded polymer strand. Regardless of the specific structure of the filament, it can be a single thread or strand or multiple woven, twisted or unwoven threads or strands, preferably of a uniform diameter substantially along the entire length of the filament. Moreover, the filament is to be cohesive and coherent along its entire length, whereby the structural integrity of the filament as well as the strength of the filament is substantially uniform along the entire length of the filament.

In addition to the desired structural integrity and uniform strength of each filament, the cross-sectional area or diameter of the filament relative to the total area of a fiber wall is of substantial importance. The greater the diameter and area of embedded filaments in a fiber wall, the smaller the fiber wall area remaining for filtration. Accordingly, the fiber wall area occupied by one or more filaments is to be balanced between suitably and effectively increasing the fiber integrity and enhancing the strength of the fiber without unnecessarily reducing or interfering with filtration effectiveness of the fiber wall. Preferably the one or more filaments will occupy less than about 15% of the fiber wall cross-sectional area, preferably 10% or less, and more preferably about 6% or less. In specific preferred embodiments, the cross sectional area occupied by one or more filaments is preferably between about 0.5% and about 5%, each of the one or more filaments having a cross-sectional area occupying between about 0.1% and about 3% of the fiber wall area, and preferably between about 0.2% and about 2% of the cross-sectional area of a fiber wall. As previously disclosed and as described in the incorporated disclosure of application Ser. No. 09/549,131, preferred fibers for plasmapheresis applications have a nominal wall thickness of between about 175 µm and about 260 µm. By way of example, with a fiber wall thickness of about 250 µm, where three filaments are used, each having a diameter of 50 µm, about 1.5% of the cross-sectional area of the fiber is occupied by filament. Where 3-75 µm filaments are used, the cross-sectional occupancy of the filaments is about 3%, and 3-100 µm filaments occupy about 6% of the fiber wall area. Although a single filament provides an adequate safety factor to prevent breakage of the fiber, the use of one or two additional filaments will increase the safety margin exponentially without significant detriment to filtration performance. By using 6-50 µm filaments occupying 2.6% of the cross-sectional fiber area, fiber strength exceeds that where 3-100 µm filaments are used even though less area of the fiber wall is occupied by the filaments. The above filament cross-sectional areas and diameters and fiber wall thickness are provided for illustration only and are not intended to limit the scope of the invention described herein.

As previously described, the one or more filaments are to be substantially uniform in strength along the entire filament length as well as to be of substantially uniform diameter or cross-sectional area. Preferably, each filament will have a tensile strength of at least about 5,000 psi and more preferably of at least about 10,000 psi. Different filament materials may be used, such as fiberglass, polypropylene, silk, polysulfone, polyethersulfone, polyimide, polyamide (nylon) and aromatic polyamide (aramid) e.g., poly-paraphenylene terephthalamide (Kevlar). However, other biocompatible materials which are chemically and physically compatible with the fiber polymer composition may also be used. For some fibers, it may be preferred to use a filament composition that is different from the polymer comprising the fiber material; in other cases the same filament and fiber material may be preferred. In either case, the filament and fiber compositions are to be compatible, such that the filament is physically and structurally cohesive with the fiber wall.

As previously discussed, the filaments are preferably embedded in the fiber wall approximately midway between the inner and outer wall surfaces. In the preferred asymmetric fibers having the different zones as previously described, preferred locations for the filaments are between Zones 2 and 4 of the fiber. Such location will maximize cohesion within the body of the fiber to yield optimum strength with minimum interference to plasma flow through the fiber from the outer surface to the inner lumen and subsequent delivery ex-vivo. Such location of a filament is shown in FIG. 1, and particularly in FIG. 2 with the filament located in Zone 3, between Zones 2 and 4 of the fiber wall. Where more than one fiber is used, it is preferred to place the fibers generally or substantially equal distance from one another as illustrated in FIGS. 4 and 5.

In a further preferred embodiment, a filter device for being implanted in a blood vessel comprises one or more elongated hollow conduits or tubes to which opposite ends of each of the microporous membrane fibers are secured whereby the interior of the one or more hollow tubes communicates with the interior of each of the elongated hollow fibers. As illustrated in FIGS. 6-8, a filter assembly includes a pair of elongated hollow tubes having the end of each of the hollow fibers, secured to and communicating with the hollow tubes. In the embodiment shown, a first end of each fiber is secured to one of the hollow tubes and a second end is secured to the other hollow tube. Each fiber is embedded with one or more filaments, as previously described. A plasma or water extraction catheter assembly includes a multiple lumen catheter, preferably a triple lumen catheter, secured to a proximal end of the hollow tubes for directing blood plasma or plasma water passing through the fiber wall and into the fiber lumen to extracorporeal treatment or collection apparatus or equipment.

In the preferred embodiment illustrated in FIGS. 6-8, a pair of elongated hollow tubes are joined side-by-side lengthwise to form the core of the filter device. The two elongated hollow core tubes 14 and 16 terminate at a distal end with a distal end plug or cap 13 formed of a material that seals the open tube ends. The tubes and end cap may be made of any suitable biocompatible material, for example, medical grade extruded urethane tubes. Other biocompatible materials include synthetic rubbers, polycarbonate, polyethylene, polypropylene, nylon, etc. The elongated hollow tubes may be secured together using suitable bonding material, adhesive compositions, etc., for example, a UV curable adhesive applied along the length between the two tubes. The length and diameter of the filter device may be selected to accommodate the vessel or vein in which it is to be implanted. Accordingly, the diameter and length of the one or more elongated hollow tubes forming the central core of the filter device are selected. A suitable tube length is between about 15 cm and about 25 cm, and preferably between about 18 cm and about 22 cm. Where a pair of core tubes is used as shown in the preferred embodiment, an outer diameter of each tube of between about 1 mm and about 3 mm is suitable. A detectable marker component, e.g., a radio opaque material, may also be bonded to the device, for example, extending along the length of the tubes to assist in implanting and/or monitoring the device especially during insertion and removal. In preparing the above-described filter device, each end of each fiber including the filament is secured to a hollow tube with an adhesive or bonding material. Such adhesion will further ensure the structural integrity and optimization of the filter. Observing FIG. 7, fiber 12 with embedded filaments 10 and 10' is secured in tubes 14 and 16 using adhesive material 24, e.g., urethane. Fiber ends 21 and 23 are shown extending into the respective tubes with the filaments coterminal with the fiber ends.

The filtration performance of such a device is a function of the filter surface of the exposed fibers whereby consideration is given to use larger diameter fibers and to maximize the number of fibers. Thus, it is desirable to use as many individual fibers along the hollow core tubes of the filter device as is practical while maintaining separation of the individual fibers to provide for fluid flow therebetween, and to maximize the amount of outer fiber surface exposed to blood flowing along the length of the filter device. Moreover, the fibers are secured along the length of the hollow tubes in such a manner as to form a fluid flow space 25 between the fibers and the tubes as shown in FIGS. 7 and 8. Again, however, the length of the filter device as well as the overall cross-sectional dimension are tailored or dictated by the blood vessel in which the device is to be used so as to avoid substantial interference with blood flow through the vessel while at the same time be efficient to achieve the intended flow rate of separated plasma.

Figure 9:
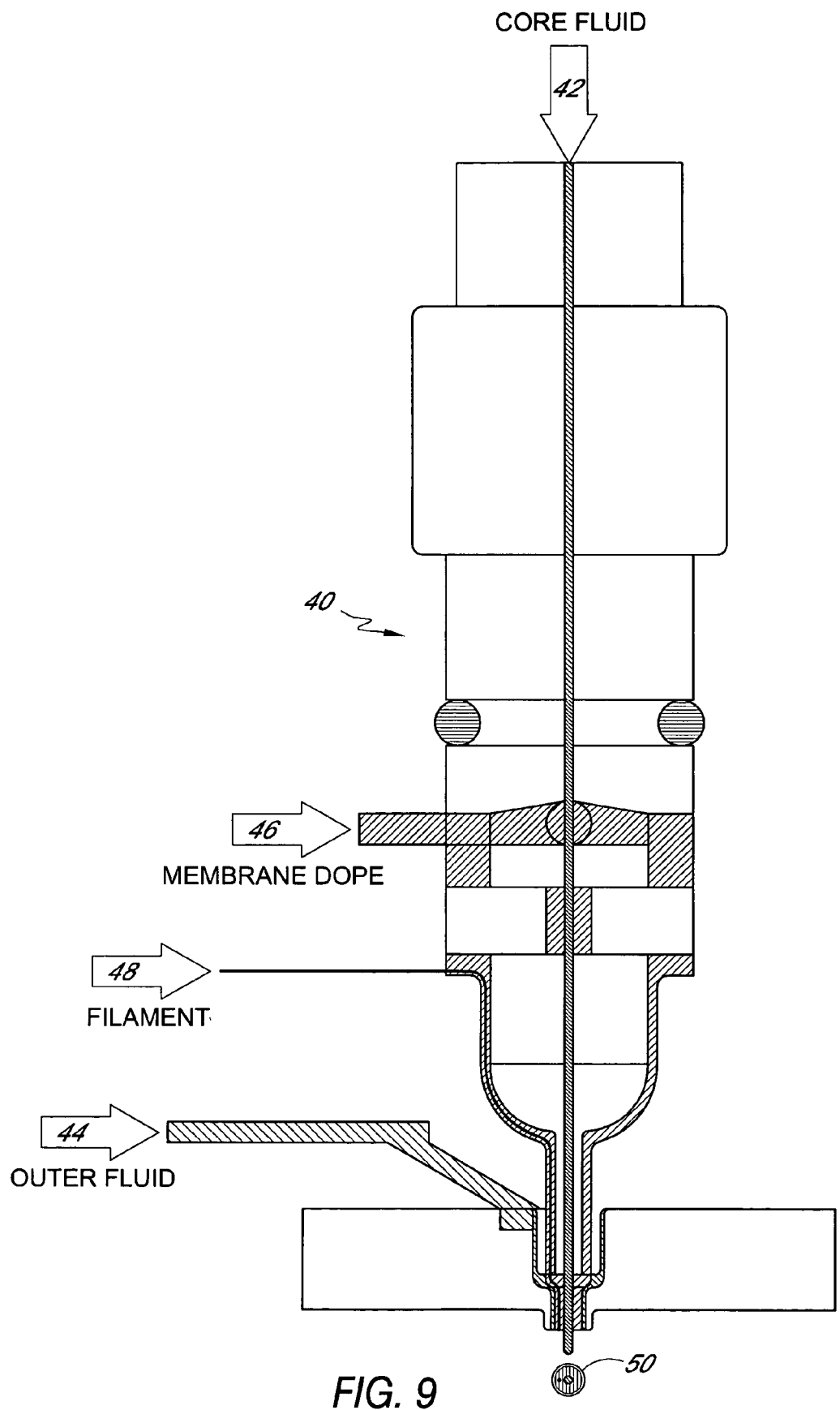
FIG. 9 is a schematic sectional view of a spinnerette for illustrating manufacture of a filament-embedded fiber described herein.

The fibers described herein may be produced using a conventional high-technology automated polymer extrusion (spinning) machine, known to those skilled in the art. In FIG. 9, a spinning die or spinnerette for extruding a fiber is illustrated. The spinnerette includes fluid passageways into which and through which different fluid and polymer compositions are directed to a final die orifice. In the example shown, a spinnerette or die 40 includes a passageway for core-forming fluid 42, a passageway for membrane-forming fluid polymer (membrane dope) 46, a passageway for outer coating fluid 44, and a passageway for introducing filament thread 48. The core-forming fluid composition is passed through the center of the die and is subsequently removed from the final assembly after the polymer fixation in a post-extrusion bath. The membrane-forming fluid polymer 46 is introduced into the die prior to the final die orifice and combined with the outer coating fluid 44 in the final stage of the die orifice prior to the fixing bath. The outer coating fluid forms Zone 1 of the previously described asymmetric hollow fiber membrane, and the membrane-forming fluid polymer forms Zones 2, 3 and 4 of the previously described fiber wall at appropriate times in fixation baths. Filament thread 48 may be introduced into the die with the membrane dope which forms the fiber body and at the same extrusion speed as the membrane-forming polymer. The filament is guided into appropriate space within the extruded membrane by guiding roller fixtures in a fixation bath augmented with limit guards (not shown). When the fiber cures and solidifies, it will have the filament embedded in the fiber wall 50 at the desired position as shown.

The elongated microporous fibers described herein in which one or more filaments are embedded are substantially improved for use in conditions, equipment, and especially blood vessels of the patient where any potential break-off and separation of a portion of the fiber could result in injurious and possibly even fatal complications. The presence of the embedded filament or filaments along the fiber length substantially obviate a condition in which fracture or breakage of the fiber along its length could result in separation of a portion of the fiber from the remaining fiber body. Moreover, by adhering each end of a filament to components such as tubes of the filter substantially avoids the likelihood of one fiber end becoming separated from the filter. In addition, the tensile strength of the fiber in which the filaments are securely embedded in the fiber wall are substantially the same as the tensile strength of the embedded filaments. These as well as other advantages of the structurally enhanced fibers as described herein will be evident to those skilled in the art.

Although the preferred fibers described herein comprise asymmetric fiber walls having microporous wall structure capable of separating plasma and plasma components from whole blood in-vivo, it should also be appreciated that other filtration fibers may be embedded with filaments for improved properties. The fibers may have symmetrical or asymmetrical fiber wall morphology. Such filament enhanced and strengthened fibers may be especially useful in apparatus and systems where fiber integrity, strength, and resistance to fiber breaks, particulation and separation are important, for example, in dialysis apparatus, bioreactors, and other medical applications as well as in industrial filtration equipment, reverse osmosis, etc. The size and number of such filaments may be selected to meet the fiber requirements desired taking into account and balancing the enhanced structural properties versus filtration performance and efficiency.

What is claimed is:

1. A filter device for being implanted in a blood vessel for carrying out in-vivo plasma separation comprising:
a plurality of elongated hollow tubes comprising one or more first and one or more second elongated hollow tubes, and a plurality of elongated fibers each fiber having a microporous membrane fiber wall with an outer wall surface and an inner wall surface defining an interior lumen extending along the length thereof wherein the fiber wall morphology of each of the elongated fibers is asymmetrical between the inner wall surface and the outer wall surface, said fiber wall having a higher mass density zone adjacent to the outer wall surface and a lower mass density zone adjacent to the inner wall surface, said higher mass density zone having a smaller average nominal pore size than the average nominal pore size in the lower mass density zone, each fiber having a first end secured to a first said elongated hollow tube and a second end secured to a second said elongated hollow tube, wherein the interior of the said plurality of elongated hollow tubes communicates with the interior lumen of each of the fibers, said fibers including one or more continuous filaments embedded in the microporous fiber wall between the first and second ends of the fiber.

2. A filter device of claim 1 comprising two of said elongated hollow tubes, each of said tubes having a plurality of holes spaced apart along a substantial portion of the length thereof, each hole receiving a first or a second end of an elongated microporous fiber.

3. A filter device of claim 1 wherein said one or more filaments extend along said fiber wall substantially uniformly between said inner wall surface and said outer wall surface.

4. A filter device of claim 1 wherein said one or more filaments extend along said fiber wall substantially equidistant between said inner wall surface and said outer wall surface.

5. A filter device of claim 1 wherein the one or more filaments have a substantially uniform tensile strength along the length thereof.

6. A filter device of claim 1 wherein said one or more filaments occupy less than about 15% of the fiber wall cross-sectional area of said fiber.

7. A filter device of claim 1 wherein said one or more filaments occupy less than about 10% of the fiber wall cross-sectional area of said fiber.

8. A filter device of claim 1 wherein each of said one or more filaments has a cross-sectional area occupying between about 0.1% and about 2% of the cross-sectional area of said fiber.

9. A filter device of claim 1 wherein each of said one or more filaments has a cross-sectional area occupying between about 0.2 and about 2% of the cross-sectional area of said fiber.

10. A filter device of claim 1 comprising a plurality of said filaments and wherein each filament has a cross-sectional area occupying between about 0.2% and about 2% of the cross-sectional area of said fiber.

11. A filter device of claim 1 wherein said one or more filaments have a tensile strength of at least about 5,000 psi.

12. A filter device of claim 1 wherein said one or more filaments comprise fiberglass, polypropylene, silk, polysulfone, polyethersulfone, polyimide, polyamide or aramid.

13. A filter device of claim 1 comprising two of said filaments.

14. A filter device of claim 13 wherein said one or more filaments comprise fiberglass, polypropylene, silk, polysulfone, polyethersulfone, polyimide, polyamide or aramid.

15. A filter device of claim 14 wherein each of said one or more filaments has a cross-sectional area occupying between about 0.2% and about 2% of the cross-sectional area of said fiber.

16. A filter device of claim 14 comprising a plurality of said filaments occupying between about 0.5% and about 5% of the cross-sectional area of said fiber.

17. A filter device of claim 16 wherein said higher mass density zone is characterized by a nominal average pore diameter of between about 0.005 μm and about 0.05 μm.

18. A filter device of claim 1 wherein the fiber wall structure comprises a continuous change in mass density from the outer wall surface to the inner wall surface.

19. A filter device of claim 18 wherein the fiber wall structure comprises a continuum of voids bounded by solid frames.

20. A filter device of claim 1 wherein said membrane fiber wall has three mass density zones and wherein each of said zones is characterized by a different average nominal pore size.

21. A filter device of claim 1 wherein said membrane fiber wall has four or more mass density zones and wherein each of said zones is characterized by a different average nominal pore size.

22. A filter device of claim 1, 20, or 21 wherein said lower mass density zone is characterized by a nominal average pore diameter of between about 1 μm and about 60 μm.

23. A filter device of claim 22 wherein said higher mass density zone is characterized by a nominal average pore diameter of between about 0.3 μm and about 1 μm.

24. A filter device of claim 1, 20, or 21 wherein said higher mass density zone is characterized by a nominal average pore diameter of between about 0.3 μm and about 1 μm.

25. A filter device of claim 1 wherein said lower mass density zone is characterized by a nominal average pore diameter of between about 2 μm and about 6 μm.

26. A filter device of claim 25 wherein said higher mass density zone is characterized by a nominal average pore diameter of between about 0.4 μm and about 0.8 μm.

27. A filter device of claim 26 having one or more intermediate mass density zones having a nominal average pore diameter of between about 0.8 μm and about 2 μm.

28. A filter device of claim 27 having two intermediate mass density zones, a first intermediate zone having a nominal average pore diameter of between about 0.8 μm and about 1.2 μm and a second intermediate zone having a nominal average pore diameter of between about 1.2 μm and about 2 μm.

29. A filter device of claim 1 wherein said higher mass density zone is characterized by a nominal average pore diameter of between about 0.4 μm and about 0.8 μm.

* * * * *